US006284532B1

(12) United States Patent
Brown et al.

(10) Patent No.: US 6,284,532 B1
(45) Date of Patent: Sep. 4, 2001

(54) PURIFIED HUMAN PAPILLOMAVIRUS

(75) Inventors: Darron R. Brown, Zionsville, IN (US); Tracy L. McClowry, Oshkosh, WI (US); Janine T. Bryan, Germantown, MD (US); Kenneth H. Fife, Xionsville, IN (US)

(73) Assignee: Indiana University, Bloomington, IN (US)

( * ) Notice: Subject to any disclaimer, the term of this patent is extended or adjusted under 35 U.S.C. 154(b) by 0 days.

(21) Appl. No.: 09/135,241

(22) Filed: Aug. 17, 1998

(51) Int. Cl.$^7$ .............................. C12N 15/37; C12N 15/63
(52) U.S. Cl. ...................................... 435/320.1; 536/23.72
(58) Field of Search ...................... 536/23.72; 435/320.1, 435/235.1, 5, 69.3

(56) References Cited

U.S. PATENT DOCUMENTS

| 4,814,268 | 3/1989 | Kreider et al. ...................... 435/239 |
| 5,437,951 | * 8/1995 | Low et al. ............................ 435/69.1 |

FOREIGN PATENT DOCUMENTS

| 9118294 | 5/1990 | (WO) ...................................... 33/569 |

OTHER PUBLICATIONS

Forslund et al, Journal of Clinical Microbiology 34:802–9, 1996.*
Brown D. R., Bryan, J. T., Cramer, H., and Fife, K. H. (1993a) *J. Clin. Microbiol.* 31(10), 2667–2673.
Brown D. R., Bryan, J. T., Cramer, H., Katz, B. P., Handy, V., and Fife, K. H. (1994a) *J. Infectious Diseases* 170(4), 759–765.
Brown D. R., Fan. L., Jones, J., and Bryan, J. (1994b) *Virology* 201(1), 46–54.
Brown D. R., Bryan, J. T., Pratt, L., Handy, V., Fife, K. H., and Stoler, M. H. (1995) *Virology* 214(1), 259–263.
Christensen N. D., Koltun, W. A., Cladel, N. M., Budgeon, L. R., Reed, C. A., Kreider, J. W., Welsh, P. A., Patrick, S. D., and Yang, H. (1997) *J. Virol.* 71(10), 7337–7344.
Ho, G. Y. F., Bierman, R., Beardsley, L., Chang, C. J., and Burk R. D. (1998) *New England J. Med.* 338(7), 423–428.
Kreider, J. W., Howlett, M. K., Lill, N. L., Bartlett, G. L., Zaino, R. J., Sedlacek, T. V., and Mortel, R. (1986) *J. Virol.* 59, 369–376.
Kreider, J. W., M.K. Howett, A.E. Leure–Dupree, R.J. Zaino and J.A. Weber. (1987) *J. Virol.* 61, 590–593.
Manos M. M., Ting, Y., Wright, D. K., Lewis, A. J., Broker, T. R., and Wolinsky, S. M. (1989) *Cancer Cells* 7, 209–214.
Manos, M. M., Waldman, J., Zhang, T. Y., Greer, C. E., Eichinger, G., Schiffman, M. H., and Wheeler, C. M. (1994) *J. Infectious Diseases* 170(5), 1096–1099.
Ong, C. K., Bernard, H. U., and Villa, L. L. (1994) *J. Infectious Diseases* 170(5), 1086–1088.
Shah K. V., Solomon, L., Daniel, R., Cohn, S., and Vlahov, D. (1997) *J. Clin. Microbiol.* 35(2), 517–519.
Forslund O. and Hansson B.G., 1996, Human Papillomavirus Type 70 Genome Cloned from Overlapping PCR Products: Complete Nucleotide Sequence and Genomic Organization. J. Clinical Microbiology 34:802–809.
Galloway, D.A. 1994, Human Papillomavirus Vaccines: A Warty Problem. Infectious Agents and Diseases 3:187–193.

* cited by examiner

Primary Examiner—Mary E. Mosher
(74) *Attorney, Agent, or Firm*—Janet E. Reed; Saul Ewing LLP (57) ABSTRACT

A live, infective stock of a new human papillomavirus, HPV IU, is provided. HPV IU is related to but distinct from HPV MM7 and HPV LVX82. An isolated nucleic acid comprising the genome of HPV IU is also provided. Methods of using HPV IU to develop and test HPV vaccines and HPV antiviral agents are also provided.

5 Claims, 2 Drawing Sheets

| | | |
|---|---|---|
| HPV IU | (6695) | GCCCAGGGACATAATAATGGCATTTGTTGGTTTAATGAGTTATTTGTTAC |
| HPV MM7 | ( 1) | GCCCAGGGACATAATAATGGCATTTGTTGGTTTAATGAGTTATTTGTTAC |
| LVX 82 | ( 1) | GCCCAGGGtCATAATAATGGCATTTGTTGGTTTAATGAGTTATTTGTTAC |
| HPV IU | (6745) | AGTTGTAGATACTACCCGCAGTACCAATATTACTATTTCAGCTGCTGCTA |
| HPV MM7 | ( 51) | AGTTGTAGATACTACCCGCAGTACCAATATTACTATTTCAGCTGCTGCTA |
| LVX 82 | ( 51) | AGTTGTAGATACTACCCGCAGTACCAATATTACTATTTCAGCTGCTGCTA |
| HPV IU | (6795) | CACAGGCTAATGAATACACAGCCTCTAACTTTAAGGAATACCTCCGCCAC |
| HPV MM7 | ( 101) | CACAGGCTAATGAATACACAGCCTCTAACTTTAAGGAATACCTCCGCCAC |
| LVX 82 | ( 101) | CACAGGCTAATGAATACACAGCCTCTAACTTTAAGGAATACCTCCGCCAC |
| HPV IU | (6845) | ACAGAGGAATATGACTTACAGGTTATATTGCAACTTTGCAAAATACATCT |
| HPV MM7 | ( 151) | ACcGAGGAATATGACTTACAGGTTATATTGCAACTTTGCAAAATACATCT |
| LVX 82 | ( 151) | ACcGAGGAATATGACTTACAGGTTATATTGCAACTTTGCAAAATACATCT |
| HPV IU | (6895) | GACCCCTGAAATTATGGCATACCTACATAGTATGAATGAACATTTATTAG |
| HPV MM7 | ( 201) | tACCCCTGAAATTATGGCATACCTACATAGTATGAATGAACATTTATTgG |
| LVX 82 | ( 201) | tACCCCTGAAATTATGGCATACCTACATAGTATGAATGAACATTTATTgG |
| HPV IU | (6945) | ATGAGTGGAATTTTGGCGTGTTACCGCCTCCCTCCACCAGCCTTGATGAT |
| HPV MM7 | ( 251) | ATGAGTGGAATTTTGGCGTGTTACCaCCTCCtTCCACCAGCCTTGATGAT |
| LVX 82 | ( 251) | ATGAGTGGAATTTTGGCGTGTTACCGCCTCCCTCCACCAGCCTTGATGAT |
| HPV IU | (6995) | ACCTATCGCTATCTGCAGTCCCGTGCTATTACCTGCCAAAAGGGTCCTTC |
| HPV MM7 | ( 301) | ACCTATCGCTATCTGCAGTCCCGTGCTATTACCTGCCAAAAGGGTCCTTC |
| LVX 82 | ( 301) | ACCTATCGCTATtTGCAGTCCCGTGCTATTACCTGCCAAAAGGGTCCTTC |
| HPV IU | (7045) | CGCCCCTGCCCCTAAAAAGGATCCTTATGATGGCCTTGTATTTGGGAGG |
| HPV MM7 | ( 351) | CGCCCCTGCCCCTAAAAAGGATCCTTATGATGGCCTTGTATTTGGGAGG |
| LVX 82 | ( 351) | CGCCCCTGCCCCTAAAAAGGATCCTTATGATGGCCTTGTATTTGGGAGG |
| HPV IU | (7095) | TTGATTTAAAGGACAAACTATCCACAGATTTAGATCAGTTTCCTTTGGGC |
| HPV MM7 | ( 401) | TTGATTTAAAGGACAAACTATCCACAGATTTgGATCAGTaTCCTTTGGGa |
| LVX 82 | ( 401) | TTGATTTAAAGGACAAACTATCCACAGATTTAGATCAGTTTCCTTTGGGa |
| HPV IU | (7145) | CG |
| HPV MM7 | ( 451) | CG |
| LVX 82 | ( 451) | CG |

PURIFIED HUMAN PAPILLOMAVIRUS

Pursuant to 35 U.S.C. §202(c), it is acknowledged that the U.S. Government has certain rights in the invention described herein, which was made in part with funds from the National Institute of Allergy and Infectious Disease.

FIELD OF THE INVENTION

The present invention relates to the field of virology and control of viral disease. In particular, the invention provides a purified, infective stock of a human papillomavirus, useful for testing and developing vaccines and other therapeutic agents.

BACKGROUND OF THE INVENTION

Several publications are referenced in this application in parentheses in order to more fully describe the state of the art to which this invention pertains. The disclosure of each of these publications is incorporated by reference herein.

Genital tract infections with human papillomaviruses (HPVs) are manifested in many ways, from an asymptomatic carrier state, to the commonly recognized disease condylomata acuminata (genital warts), and to overt malignancy. Infections with certain genital HPVs, such as HPV types 6 and 11 cause external genital warts, a condition characterized by marked epithelial proliferation and a low risk of dysplastic changes. In contrast, other genital HPVs including types 16, 18, and 31 are highly associated with dysplastic cervical lesions. These dysplasia-associated, or "high risk" HPV types can be detected in external genital warts removed from immunosuppressed patients. About half of the lesions from immunosuppressed patients contain a high risk HPV type, often in a mixed infection with a "low risk" type such as HPV type 6 or 11.

For an HPV to be assigned a type number, the entire genome must be cloned and three gene regions (E6, E7, and L1) must be sequenced and compared to known types. With the advent of consensus primer PCR amplification for detection of HPV DNA in clinical specimens, it has become clear that there are a significant number of HPVs in addition to the numbered types. The most commonly used consensus PCR system uses degenerate primers located in a conserved region of the L1 (major capsid) gene to amplify a segment of about 450 base pairs. A number of HPV sequences have been found which do not match well with any of the known (numbered) HPV types. These are usually designated by an arbitrary name assigned by the group that first recognized it. In some cases, the same or closely related sequences are independently reported by different groups and given different names. While these almost certainly represent novel HPV types, they are designated by these "unconventional" names until the full genome is cloned and characterized. Several of the uncharacterized HPVs have been identified in specimens from immunocompromised patients.

One such partially characterized HPV is HPV MM7 (also called Pap 291) (Manos, M. M., Waldman, J., Zhang, T. Y., Greer, C. E., Eichinger, G., Schiffman, M. H., and Wheeler, C. M. (1994) *J. Infectious Diseases* 170(5), 1096–1099). This virus type is closely related to HPV LVX82 (Ong, C. K., Bernard, H. U., and Villa, L. L. (1994) *J. Infectious Diseases* 170(5), 1086–1088), and the two are sometimes referred to as HPV MM7/LVX82. Infection with this HPV type appears to be relatively common compared to other genital HPVs. All published studies that have identified HPV MM7/LVX82 have been performed on cervical lavage or cervical biopsy samples rather than in DNA extracted from genital warts. In one study, HPV MM7/LVX82 was identified in 20 of 338, or 5.9% of cervical samples from patients with low grade dysplasia, and 1 of 43, or 2.3% of high grade dysplasia samples. In a study of cervical HPV acquisition by college women, incident infection with HPV MM7/LVX82 (called Pap 291 in this study) was identified in 15 of 529, or 2.8% of women followed over a period of two years, making it one of the more common types acquired (Ho, G. Y. F., Bierman, R., Beardsley, L., Chang, C. J., and Burk, R. D. (1998) *New England J. Med.* 338(7), 423–428).

In another study, 22 HPV types were identified in cervical lavage samples of human immunodeficiency virus (HIV)-seropositive women, and seven types in lavage samples from HIV-seronegative women (Shah K. V., Solomon, L., Daniel, R., Cohn, S., and Vlahov, D. (1997) *J. Clin. Microbiol.* 35(2), 517–519). Overall, 104 of 150, or 69.3% of HIV-seropositive women had detectable HPV compared to 19 of 72, or 26.4% of HIV-seronegative women. The most prevalent HPV type detected in both groups of women was HPV MM7/LVX82, accounting for 20 of 150, or 13.3% of HIV-seropositive women and five of 72, or 6.9% of HIV-seronegative women. Of the 123 women with detectable HPV of any type, HPV MM7/LVX82 was the most common type detected, present in 20% of samples.

The development of vaccines against human papillomaviruses (HPV) has been hampered by the lack of a conventional culture system because HPV completes its life cycle only in fully differentiated human tissue. To overcome this obstacle, the athymic mouse xenograft system has been used to study the pathogenesis of HPV 11, and to attempt to develop neutralizing assays for vaccine development (Kreider, J. W., M. K. Howett, A. E. Leure-Dupree, R. J. Zaino and J. A. Weber. (1987) *J. Virol.* 61, 590–593; Kreider, J. W., Howlett, M. K., Lill, N. L., Bartlett, G. L., Zaino, R. J., Sedlacek, T. V., and Mortel, R. (1986) *J. Virol.* 59, 369–376). In this method, an extract from HPV-infected tissue is used to infect human foreskin fragments, which are then implanted under the renal capsules of athymic mice. After ascertaining that an implant is HPV infected, the virus contained in the implant is propagated by additional rounds of xenograft implantation into athymic mice. Recently, HPV 40 has been produced in this system (Christensen N. D., Koltun, W. A., Cladel, N. M., Budgeon, L. R., Reed, C. A., Kreider, J. W., Welsh, P. A., Patrick, S. D., and Yang, H. (1997) *J. Virol.* 71(10), 7337–7344). Production of an isolate consistent with HPV MM7/LVX82 was also reported. However, an infectious stock of HPV MM7/LVX82 was not obtained. HPV 16 has been produced using a similar system, implanting into mice with severe combined immune deficiency (SCID).

From the foregoing discussion, it is clear that live, infectious stocks of a variety of types of human papillomavirus are needed in order to produce and test broad spectrum vaccines against these viruses. It is particularly important that such a vaccine is targeted to commonly found HPV types, such as the MM7/LVX82. At present, only a small number of HPV types, HPV 11, HPV 40 and HPV 16, are available as infectious stocks. Accordingly, it is an object of the invention to provide a live, infectious stock of HPV MM7/LVX82. It is a further object of the present invention to provide vaccines directed against HPV MM7, HPV LVX82 and similar types, as well as methods for testing the ability of those vaccines to elicit an appropriate immune response against the selected HPV types.

SUMMARY OF THE INVENTION

According to one aspect of the present invention, a live, infective stock of a human papillomavirus (HPV) of type HPV MM7/LVX82 is provided. This virus stock is substantially free of other HPV types. The live, infective HPV stock comprises a novel human papillomavirus, referred to herein as HPV IU. HPV IU is related to, but distinct from HPV MM7 and HPV LVX82.

According to another aspect of the invention, an isolated nucleic acid comprising the genome of an HPV MM7/LVX82 type is provided. In a preferred embodiment, the genome is an HPV IU genome. HPV IU genomic DNA was deposited with the American Type Culture Collection Patent Depository (10801 University Blvd., Manassas Va., 20110–2209) on May 23, 2001, and assigned ATCC designation PTA-3403 (Human Papillomavirus Genomic DNA: MM7/LVX82. In a particularly preferred embodiment, the genome comprises the sequence of SEQ ID NO:1.

According to another aspect of the invention, a recombinant expression vector is provided, in which is inserted a nucleic acid sequence comprising part or all of the aforementioned HPV MM7/LVX82 genome. An antigenic epitope, or a virus-like particle, produced by expression of part or all of this genome are also provided.

According to another aspect of the invention, a vaccine for immunization against human papillomavirus is provided, comprising the antigenic epitope or virus-like particle produced by expression of the HPV MM7/LVX82 genome or part thereof.

According to another aspect of the invention, a method of testing a candidate HPV vaccine for its ability to elicit a HPV-neutralizing immune response in a mammal (human or animal) is provided. The method comprises: (a) providing serum from a mammal immunized with the candidate vaccine; (b) providing a live, infectious stock of HPV of type MM7/LVX82 (preferably HPV IU); (c) contacting an implantable tissue with the infectious HPV IU, in the presence or absence of the serum; (d) implanting the tissue into an animal host in which the implantable tissue has been determined to grow, and HPV infection of the tissue to occur over a pre-determined time period; and (e) comparing HPV infection in the implanted tissue contacted with the infectious HPV in the presence of the serum with HPV infection in the implanted tissue contacted with the infectious HPV in the absence of the serum. A reduction in HPV infection in the presence of the serum is indicative of the ability of the candidate vaccine to elicit a HPV-neutralizing immune response in the mammal.

According to another aspect of the invention, a method is provided for testing antiviral agents directed against HPV, particularly HPV of the MM7/LVX82/IU type. The method comprises (a) providing a live, infectious stock of HPV of the MM7/LVX82 type; (b) contacting an implantable tissue with the infectious HPV, in the presence or absence of the candidate antiviral agent; (c) implanting the tissue into an animal host in which the implantable tissue has been determined to grow, and HPV infection of, and replication in, the tissue to occur over a pre-determined time period; and (d) comparing HPV infection or replication in the implanted tissue contacted with the infectious HPV in the presence of the candidate antiviral agent with HPV infection or replication in the implanted tissue contacted with the infectious HPV in the absence of the candidate antiviral agent, a reduction in HPV infection in the presence of the agent being indicative of the ability of the candidate antiviral agent to reduce or prevent HPV infection or replication in the mammal.

These and other features and advantages of the present invention will be described in greater detail in the description and examples set forth below.

BRIEF DESCRIPTION OF THE DRAWINGS

FIG. 1. Sequence alignment of HPV IU consensus primer region (bases 6695–7146 of SEQ ID NO:1) with two previously described HPVs designated MM7 (SEQ ID NO:2) and LVX 82 (SEQ ID NO:3). Positions in which HPV IU differs from one or both sequences are shown in bold. Regions corresponding to the degenerate primers are indicated by a line above the sequence.

DETAILED DESCRIPTION OF THE INVENTION

I. Definitions

Various terms relating to the biological molecules of the present invention are used hereinabove and also throughout the specification and claims.

With reference to nucleic acids, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived; or, if the nucleic acid comprises an entire genome (such as a viral genome), it has been isolated from a virus particle in which it naturally occurs, and inserted into a heterologous DNA molecule. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies, the term "immunologically specific" refers to antibodies that bind to one or more epitopes of a protein of interest, but which do not substantially recognize and bind other molecules in a sample containing a mixed population of antigenic biological molecules. As used herein, the term "antigenic epitope" refers to a sequence of a protein that is recognized as antigenic by cells of the immune system and against which is then directed an immune response, such as an antibody response, for example.

As used herein, the term "open reading frame" refers to a length of nucleic acid sequence, between a translation start codon and any one or more of the known termination codons, which can be translated potentially into a polypeptide sequence. An open reading frame is sometimes referred to herein as a "coding region", since it has the potential to encode a polypeptide.

The term "operably linked" means that the regulatory sequences necessary for expression of the coding sequence are placed in a DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression cassette.

As used herein, the term "expression vector" refers to a plasmid, viral vector, or other vector comprising a sequence desired to be expressed, or an insertion site for such sequence, operably associated with any and all 5' and 3' regulatory sequences necessary for expressing the desired sequence. The terms "expression" or "expressing" refer to the production of an encoded product of the sequence desired to be expressed, which is usually a protein or peptide, but which could be an RNA molecule.

As used herein, the term "capsid coding region" refers to that region of a viral genome that contains the DNA or RNA code for protein subunits that are packaged into the protein coat of the virus particle.

The term "virion" refers to a virus particle that contains both the capsid protein and the viral genome. Accordingly, a virion is an infectious particle.

The term "virus-like particle" refers to a particle that comprises only the viral capsid, and therefore is not infectious.

II. Description

An infectious stock of HPV IU, a genital human papillomavirus related to HPV MM7/LVX82, is provided in accordance with the present invention. The preparation of this infectious stock is summarized below and described in detail in Example 1. The successful propagation of a substantially pure stock of HPV IU using the mouse xenograft system is surprising and unexpected, in view of the failure of others (e.g, Christensen et al., 1997, supra) to propagate an HPV MM7/LVX82 type using the same system. Without intending to be limited by any explanation, it is believed that the inventor's success in propagating a substantially pure HPV MM7/LVX82 type resulted from repeated screenings of samples from immunosuppressed patients (accompanied by numerous failures in identifying a propagatable HPV MM7/LVX82 type), until a particular sample was collected comprising a sufficiently high titer of the virus to enable its successful propagation in the athymic mouse xenograft system.

To identify and isolate additional genital HPV types for use in development of vaccines and elucidation of HPV biology, condylomata acuminata lesions containing a high copy number of HPV and detectable L1 major capsid protein were used to prepare infectious virus stocks. Human foreskin fragments were infected with the virus preparations and implanted under the renal capsules of athymic mice. After five months of growth, implant tissue was removed and processed for studies to detect HPV infection. Evidence of HPV infection was noted in some of the implants, but in contrast to HPV 11-infected epithelium, the implants derived from the new virus preparations contained a lesser degree of acanthosis; less developed koilocytosis; and a reduced number of preserved nuclei in the hyperkeratotic material within the cyst lining.

The L1 consensus region was amplified by polymerase chain reaction (PCR) from implant DNA and sequenced. Alignment of the amplified sequences with those in the HPV sequence database showed that the 452 bp amplimer was closely related, but not identical to HPV LVX82 and HPV MM7 (also called Pap 291). Within the 452 bp region, the HPV IU sequence differed at four positions from the HPV LVX82 sequence and at six positions from the HPV MM7 sequence (FIG. 1). However, translation of all three sequences revealed an almost identical 150 amino acid sequence, indicating that HPV IU, HPV MM7 and HPV LVX82 are sequence variants of a single, as yet unnumbered, HPV type.

Figure 2:
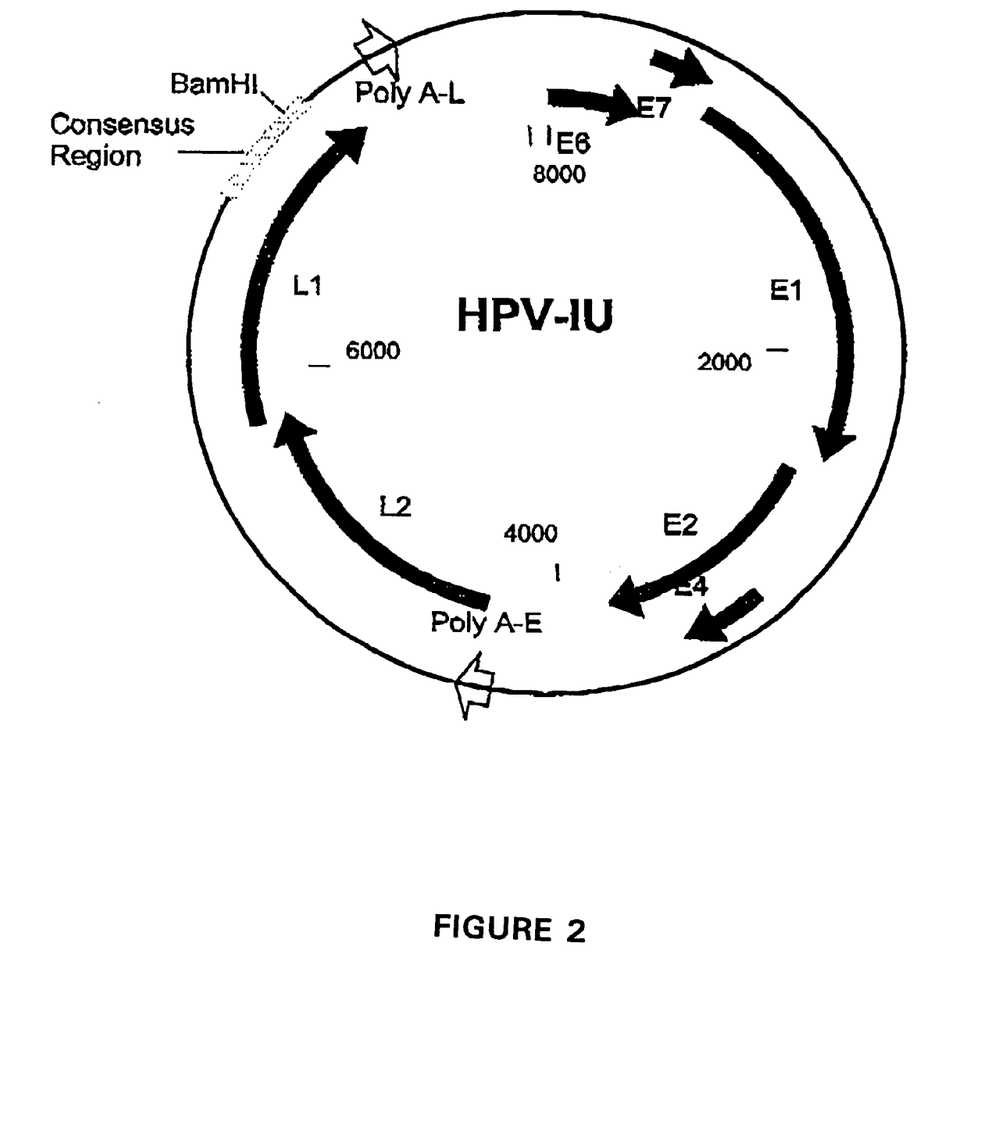
FIG. 2. Predicted genetic map of the HPV IU genome (SEQ ID NO:1), showing the major putative early and late open reading frames, early and late polyadenylation signals, and the location of the consensus primer 452 base pair region within the L1 open reading frame.

The entire genome of HPV IU was amplified by PCR and cloned. The sequence of the HPV IU genome is set forth herein as SEQ ID NO:1, and the genome depicted schematically in FIG. 2.

The presence of virions of the new isolate, HPV IU, in the implants was verified by immunohistochemical detection of L1 major capsid protein and by demonstration of virion particles by electron microscopy. A second extract was made from one of the new implants and used to successfully propagate HPV IU.

Several lines of evidence indicate that the HPV IU-infected implants were substantially, if not completely, free of other HPV types. First, a total of eight implants were examined by PCR and subsequently sequenced; all amplimers contained the identical HPV IU sequence. Second, the low stringency Southern blot using probes of HPV types 6, 11, 16, and 18 yielded bands adding up to the approximate size of an HPV genome. These bands did not match the PstI pattern of any common genital HPV type. Third, the high stringency Southern blot using the HPV IU whole genomic probe yielded a PstI restriction pattern identical to that of the low stringency blot. Fourth, the DNA in situ assay was negative for HPV types 6, 11, 16, 18, 31, 33, and 35. Finally, the hybrid capture assay was negative for the 14 types commonly found in genital tract infection.

Because HPV MM7/LVX82 appears to be a relatively common genital type, especially in immunocompromized women, the number of cases of cervical abnormalities caused by this type is likely to be relatively large. A preferred method of reducing the incidence of genital tract HPV infection is development of effective vaccines. It is likely that type-specific vaccines will be required to protect against the many HPVs known to exist. To prepare effective type-specific vaccines, it is necessary to identify, sequence, and establish neutralization assays for prevalent genital HPV types. Recently identified and uncharacterized HPVs such as HPV MM7/LVX82 and HPV IU are clearly of medical importance, given their prevalent distribution, especially in immunocompromised women. In addition to the well characterized genital HPVs such as HPV types 6 and 16, many of these newly identified types should also be included in effective vaccines.

Live, infective stocks of HPV IU are prepared by grinding the infected mouse tumor tissue in an appropriate buffer, e.g., phosphate-buffered saline, then freezing the tissue suspension. The live, infective HPV IU stock provided in accordance with the present invention is used to produce and/or test a vaccine, or a component of a multi-target vaccine, to elicit neutralizing antibodies against different HPV types. Such vaccines are expected to elicit an immune response against HPV IU and variants thereof, such as HPV MM7 and HPV LVX82, among other variants which have not yet been identified.

Infective stocks of HPV IU can be used in any standard methodology to test candidate vaccines directed to HPV. In a preferred embodiment, the neutralization assay in athymic mouse xenografts described by Bryan et al. (J. Med. Virol. 53: 185–188, 1997) is used. The steps are as follows. First, HPV IU virions are purified by cesium gradient centrifugation from the HPV-infected foreskin tissue described above. The protein content of the HPV IU preparation is determined by measuring the total protein content of the preparation, then estimating the percentage of the major capsid (L1) protein in the preparation using SDS polyacrylamide gel electrophoresis and immunoblotting with anti L1-serum.

To prepare polyclonal antisera against HPV IU, rabbits are immunized with an appropriate amount, e.g., 10 ng, of non-denatured virions emulsified in an adjuvant, such as Freund's adjuvant, followed by four booster immunizations of an equivalent amount of antigen in incomplete adjuvant, given at two-week intervals after the first immunization. Sera from the rabbits are collected about nine weeks after immunization. The amount of anti-HPV IU IgG in the rabbit serum is quantified by capture ELISA (enzyme-linked immunosorbent assay), using HPV IU virus-like particles (VLPs), prepared as described below.

To perform the neutralization assay, foreskin tissue is obtained from routine circumcision, the dermis is removed, and the remaining epidermal tissue is cut into small fragments. Tissue fragments are added to a tube containing medium in which is dispersed a known quantity of HPV IU virions, along with various dilutions of the antiserum (including a control in which no antiserum is added). Following a short incubation at 37° C., the fragments are implanted under the renal capsules of athymic mice. To ensure HPV infection adequate for detection, mice are not killed until 10 weeks after implantation. Implants are then removed from the mice, measured and placed in formalin solution for preparation of paraffin-embedded sections.

For the DNA in situ assay to detect the presence or absence of HPV IU infection, the sections of foreskin implants are deparaffinized and processed with the Digene Tissue Hybridization Kit (Digene Diagnostics, Beltsville Md.) according to manufacturer's instructions. Following deparaffinization, sections are hybridized with a biotinylated HPV IU DNA probe. Detection of the hybridized probe is performed by incubation of slides with a streptavidin-alkaline phosphatase conjugate, followed by reaction with a colored product-forming substrate. Cells positive for HPV DNA are identified as purple nuclear-staining of differentiated epithelial cells in the foreskin implants by light microscopy. Neutralization of HPV IU is demonstrated by an absence of HPV DNA in the DNA in situ hybridization assay.

HPV IU virions are also used to screen for antiviral agents (see, e.g., Kreider et al., Antiviral Res. 14: 51–58, 1990). This is accomplished using the mouse xenograft system in a manner similar to that described above for identifying neutralizing antibodies. Infection and implantation is carried out in the presence or absence of a candidate antiviral agent, and the effect of the agent on subsequent infectivity and replication of the virus in the graft tissue is observed.

The genome of HPV IU has been cloned and sequenced in accordance with the present invention. This material is used to produce an HPV IU vaccine, for use alone, or as part of a multi-component HPV vaccine. A preferred method for developing such a vaccine is to subclone a segment of the genome encoding a particularly antigenic component of HPV, such as the major (L1) capsid protein, and thereafter expressing capsids or virus-like particles in a suitable eucaryotic expression system, such as vaccinia virus or baculovirus, among others. Expressed capsids or VLPs are purified and used as vaccines to elicit a neutralizing immune response in persons at risk of HPV infection (for a review of HPV VLPs and their uses, see Hagensee & Galloway, Papillomavirus Report 4: 121–124, 1993).

The following specific example is provided to illustrate embodiments of the invention. It is not intended to limit the scope of the invention in any way.

EXAMPLE 1

Identification and Characterization of HPV IU and Propagation in Athymic Mouse Xenograft System To identify and characterize additional genital HPV types for elucidation of HPV pathogenesis and development of vaccines, an extract was prepared from genital lesions removed from immunosuppressed patients, pregnant women, and from patients with large lesions containing L1 protein. This example describes the identification of a new HPV isolate (HPV IU) from this source, and its successful propagation in the athymic mouse xenograft system.

Materials and Methods

Preparation of virus extract from tissue. Thirty-three excision biopsies of exophytic condylomata acuminata lesions were performed as previously described (Brown D. R., Bryan, J. T., Cramer, H., Katz, B. P., Handy, V., and Fife, K. H. (1994a) *J. Infectious Diseases* 170(4), 759–765). All of the biopsy samples were analyzed by Southern blot analysis or hybrid capture for detection of HPV DNA (Brown D. R., Bryan, J. T., Cramer, H., and Fife, K. H. (1993a) *J. Clin. Microbiol.* 31(10), 2667–2673). Twenty-seven of the lesions were removed from patients with conditions known to be associated with defects in cellular immunity. Nine of the lesions were removed from patients who were iatrogenically immunosuppressed following transplantation of kidney or liver; seven were removed from patients infected with the human immunodeficiency virus (HIV); and eleven were from pregnant women. The remaining six patients were not immunosuppressed or pregnant, but had unusually large genital lesions, thus providing abundant infected tissue.

Lesions from these 33 patients were combined in a large polypropylene tube with 100 ml of Solution 1, (50 mM $NaPO_4$ (di/mono) pH 8.0, 200 mM NaCl, 10 mM EDTA) prechilled to 4° C. Using a Biosonik IV tissue homogenizer (Bronwill, Rochester, N.Y.) on the lowest setting, the tumor tissue was homogenized to a thick suspension and the extract chilled on ice. The tissue extract was centrifuged for five minutes at 5000×g at 4° C. The supernatant was collected and stored on ice. An additional 50 ml of Solution 1 was added to the pellet, and ultracentrifugation was repeated as above. The two low speed supernatants were combined and diluted with an additional 50 ml of Solution 1, and ultracentrifuged at 20,000×g at 4° C. for two hours to pellet HPV. The supernatant was discarded, and the resulting high speed pellet was suspended in 5 ml of Solution 2 (50 mM $NaPO_4$ (di/mono) pH 7.4, 10 mM NaCl, 10 mM EDTA).

Half of this suspension derived from the high speed pellet was reserved ("high speed pellet"), and to the other half, CsCl was added to a density of 1.34 g/ml. Centrifugation was performed at 50,000×g at 20° C. for 18 hours. A faint band was visualized by shining a small light up through the bottom of the tube. This band was removed using an 18 gauge needle. Additional Solution 2 plus CsCl was added to a density of 1.34 g/ml, and centrifugation was repeated. A visible band was removed and dialysis was performed against three changes of phosphate buffered saline, pH 7.4, and the resulting banded virus preparation was stored at −70° C.

Infection and implantation of tissue into athymic mice. Infection of human foreskin fragments and growth in athymic mice was performed as described originally by Kreider et al (1986, 1987) with slight modifications as previously described (Brown D. R., Bryan, J. T., Pratt, L., Handy, V., Fife, K. H., and Stoler, M. H. (1995) *Virology* 214(1), 259–263). Experiments were performed using the two preparations described above (high speed pellet suspension and banded virus), using eight athymic mice for each virus preparation. Additional experiments were performed using extracts from tumors resulting from the first experiments to demonstrate propagation of virus in the athymic mouse xenograft system. Mice were sacrificed 150 days after implantation of foreskin fragments.

Light microscopy, immunohistochemistry, and electron microscopy. A portion of each implant was placed in zinc formalin, and paraffin-embedded sections were prepared. One section was stained with hematoxylin and eosin. Histologic evaluation of sections was performed, using uninfected implant tissue and HPV 11-infected human foreskin implants grown in athymic mice for 150 days for comparison (Brown D. R., Fan, L., Jones, J., and Bryan, J. (1994b) *Virology* 201(1), 46–54). Additional sections were deparaffinized and used to detect L1 protein with a rabbit polyclonal antiserum raised against a bacterially expressed HPV 11 trpE/L1 fusion protein, as previously described (Brown et al., 1994b). This antiserum has been shown in our laboratory to react with L1 protein from several HPV types. Preimmune rabbit serum was used as control serum. Antibody binding was detected using the Vectastain ABC Kit (Novocastra, Newcastle upon Tyne, UK). Positive cells for L1 protein were identified by brown staining of nuclei in differentiated keratinocytes. For electron microscopy, a portion of an implant was fixed in 3% glutaraldehyde, and the tissue was embedded and sectioned. Sections were stained with uranyl acetate.

Hybrid capture assay and Southern blots. DNA was extracted from implants as previously described (Brown et al., 1993a). The hybrid capture assay, marketed as ViraType Plus® by Digene Diagnostics, Beltsville, Md. was used to detect HPV sequences in the implants (Brown et al., 1993a). HPV probes were used in two pools whose composition was based on the association of each type with genital tract malignancy. Probe group A contained the "low risk" HPV types 6, 11, 42, 43, and 44 while probe group B contained the "high risk" HPV types 16, 18, 31, 33, 35, 45, 51, 52, and 56.

For Southern blots, genomic DNA from an implant that contained histologic features of HPV infection was digested with one of several restriction endonucleases: PstI, BamHI, HincII, EcoRI, or no added restriction endonuclease. The probes used in the first Southern blot (low stringency) were a mixture of HPV types 6b, 11, 16, and 18, all cut from pUC 19 and gel purified. Southern blots were performed as previously described (Brown et al., 1993a). For the low stringency blot, prehybridization, hybridization, and washes were performed at 55° C. A second Southern blot was performed at high stringency conditions (65° C. hybridization and wash) using the PCR-amplified whole genome of the new isolate, HPV IU, as a probe (see below).

Consensus primer PCR, cloning and sequencing. PCR was performed using the primer pair My09/My11 to amplify HPV sequences in genomic DNA extracted from a total of eight athymic mouse implants (two from the initial experiments and six from the propagation experiments) (Manos M. M., Ting, Y., Wright, D. K., Lewis, A. J., Broker, T. R., and Wolinsky, S. M. (1989) *Cancer Cells* 7, 209–214). A total of 250 ng of DNA from each implant was used as template for each of eight individual PCRs. The resulting 452 base pair (bp) amplimers were cloned into pCR3.1 (Invitrogen, Carlsbad, Calif.) and DNA sequencing was performed.

Amplification and cloning of the entire HPV IU genome and DNA in situ assay. To amplify and clone the genome of HPV IU, total DNA was isolated from an implant containing histologic features suggesting HPV infection. PCR was performed using the Extend Long PCR Kit as instructed by the manufacturer (Boehringer Mannheim, Indianapolis, Ind.). This PCR system uses tow polymerases, one without proofreading (Taq) and one with proofreading (Pwo). The primer pair was designed using the 452 bp sequence amplified with L1 consensus primers. The primers were 5' CAG TAG GAT CCT TAT GAT GGC TTG TAT TTT GGG AGG TTG AT (SEQ ID NO:4) and 3' GCT ATG GAT CCT TTT TAG GGG CAG GGG CGG AAG GA (SEQ ID NO:5). Conditions for PCR were 94° C. for 30 seconds, 66° C. for 30 seconds, and 68° C. for twelve minutes, for a total of 38 cycles. Agarose electrophoresis revealed a band of approximately 7.9 kilobase pairs (kb) which was excised from the gel and purified with Gene Clean as instructed by the manufacturer (Bio 101, Vista, Calif.).

The 7.9 kb amplified DNA fragment was cloned into the Expand Vector 1 (Boehringer Mannheim) as directed by the manufacturer. This cloning method facilitates cloning of large PCR products by size selection of PCR fragments provided by the lambda packaging system, eliminating cloning of small DNA fragments. To prepare a probe for DNA in situ hybridization, the fragment was removed from the vector by BamHI endonuclease digestion and gel purification. Nick translation of the fragment was performed with the BioNick kit (Life Technologies, Gaithersburg, Md.) to biotinylate the probe. DNA in situ hybridization was performed using this biotinylated probe with the PathoGene Kit as directed by the manufacturer (Enzo Diagnostics, Farmingdale, N.Y.). Positive cells were identified by blue staining of nuclei in differentiated keratinocytes.

RESULTS

Gross and microscopic characterization of HPV-infected implants. In an effort to propagate additional HPV types, an extract was made from 33 lesions known to contain large quantities of HPV DNA and HPV L1 capsid protein. Hybrid capture analysis of the high speed pellet and the banded virus preparation showed that abundant viral DNA was present for the A and B probe groups. Probe group A contained the "low risk" HPV types 6, 11, 42, 43, and 44 while probe group B contained the "high risk" HPV types 16, 18, 31, 33, 35, 45, 51, 52, and 56. Each of these preparations were used to infect human foreskin fragments which were then implanted into athymic mice. Mice were sacrificed 150 days after implantation of foreskin tissue, and implants were removed from the mice. Four implants from the first experiment, two using the high speed pellet and two using banded virus, appeared much larger with a rougher texture than the other twelve implants. The larger tumors appeared to adhere to the kidney surface and extend outward, clearly demarcated from the mouse kidney tissue. When cut transversely, the implants were thin walled and contained solid, dry cellular debris.

Uninfected and HPV 11-infected implants grown in athymic mice were used as controls for comparison of histology. In the uninfected control implants grown for 150 days, the epithelial tissue consisted of a single basal layer with four to six additional layers of flattened intermediate squamous cells and a thin granular layer. Cellular debris and keratinized material was present in the center of the implant. No nuclei were present in the material in the center of the implant. In contrast, the HPV 11-infected implant demonstrated marked epithelial thickening (acanthosis). The parabasal layer was expanded and involved approximately one-third of the epithelium. Papillomatosis (papillary projections of the epidermis forming a microscopically undulating surface) was present, with invagination from the underlying stroma by fibrovascular supports. The suprabasal layer of the HPV 11-infected implant contained well developed koilocytes containing nuclei that were enlarged two to three times compared with nuclei of suprabasal cells in uninfected implants. Marked parakeratosis (retention of nuclei in cells of the stratum corneum) was observed as well as accumulation of cellular debris and hyperkeratotic material within the implant. In addition, nuclei were present in abundance in the shed material in the center of the implant.

In implants infected with HPV IU, there were areas of mild parabasal hyperplasia with increased mitotic activity. While epithelial thickening was noted compared to the uninfected implant, HPV IU implants were significantly less acanthotic than the HPV 11 implant after the same 150 days of growth. In addition, hypergranulosis (an abundance of granular cytoplasmic structures) and mild parakeratosis were present. Similar to the HPV 11-infected implant, the epithelium was abnormal throughout, with marked nuclear enlargement in the suprabasal and subcorneal zones. Nuclei were at least three times enlarged compared to normal suprabasal cell nuclei. Koilocytotic vacuole development was present although not nearly as flagrant as was seen in the HPV 11-infected implant. For subcorneal cells, a higher nuclear to cytoplasmic ratio was observed in the HPV IU-infected implant compared to the HPV 11-infected implant. Basal cell crowding was seen, occasionally very focal in nature. In addition, parakeratosis was observed as well as accumulation of cellular debris and hyperkeratotic material within the implant. In contrast to the HPV 11-infected implant, very few nuclei were present in the center of the HPV IU-infected implants.

In summary, the main histologic differences between the implants infected with HPV IU and the HPV 11-infected implant were 1) a lesser degree of acanthosis in the implants infected with the new virus preparation; 2) less developed koilocytosis in the implants infected with the new virus; and; 3) a markedly reduced number of preserved nuclei present in the hyperkeratotic material within the implants infected with HPV IU compared to HPV 11-infected implants.

Expression of HPV capsid antigen and whole virus. Immunohistochemical assays were performed using a polyclonal antiserum against a bacterially-expressed HPV 11 trpE-L1 fusion. Dark brown staining of nuclei of differentiated keratinocytes was seen in implants containing histologic abnormalities described above. By analogy with other papillomavirus systems, this observation suggests that the most differentiated cells were making capsid protein and were likely to be producing virus particles.

Electron microscopy was performed to verify the production of virions. Electron micrographs revealed abundant particles of approximately 50 nm in the nuclei of numerous differentiated cells. These particles resembled typical icosahedral papillomavirus. Both apparently full (appearing dense and dark) and empty (appearing less dense) capsids were observed.

Detection and characterization of HPV IU DNA. Hybrid capture analysis was performed as a screen for common genital HPV types on DNA purified from HPV IU-infected implants with abnormal histology. These studies were negative with both the A and B probe groups, indicating that a common genital HPV type was not present in the new implants.

Southern blot analysis was performed at low stringency using a mixture of HPV types 6b, 11, 16, and 18 genomic DNAs as probes. The low stringency Southern blot analysis of PstI-digested DNA from implants infected with HPV IU showed faint bands of approximately 2900, 1600, 1200, 900, 800 bp after exposure of the autoradiogram for seven days. As controls, a high copy number sample containing HPV 6c and a low copy number condylomata acuminata lesion containing HPV 16 were included in the blot. The faint bands seen in the seven day exposure did not correlate with any PstI restriction patterns for HPV types commonly associated with genital warts.

L1 consensus primers were used to amplify HPV sequences from the new implants and the amplimers were cloned and sequenced. Alignment of the amplified sequences with those in the HPV sequence database showed that the 452 base pair PCR product was nearly identical to HPV LVX82 (Ong, Bernard, and Villa, 1994) and HPV MM7 (also called Pap 291) (Manos et al., 1994), two uncharacterized (and unnumbered) HPVs (FIG. 1). Eight independent clones from both initial and passaged implants were sequenced and were identical to each other. All eight differed at four positions (outside of the degenerate primer region) from the HPV LVX82 sequence and at six positions from the HPV MM7 sequence. However, translation of all three sequences yielded an identical 150 amino acid sequence (with the exception of one change encoded in the primer region). It is therefore likely that HPV LVX82, HPV MM7, and the new isolate, HPV IU, represent sequence variants of a single yet unnumbered HPV type.

Using PCR primers extending outward from the L1 consensus primer region, the entire genome of HPV IU was amplified, cloned and sequenced (FIG. 1; SEQ ID NO:1). The full length DNA was then used as a probe for high stringency Southern blotting. A similar PstI pattern was visualized in the high stringency blot as was seen on the low stringency blot, with an obvious doublet present of approximately 800 and 900 bp. The sum of PstI restriction fragments was very close to 7900 bp, with bands corresponding to approximately 2900, 1600, 1200, 900, 800 and 500 bp. Digestion with BamHI resulted in a single band at 7.9 kb, though sequencing revealed that the HPV IU genome is actually about 8100 base pairs, one of the largest HPV genomes. Digestion with HincII resulted in a dark, wide band at approximately 4 kb, suggesting that two bands of nearly equal size were generated from episomal HPV DNA. This indicated the presence of two HincII sites in the HPV IU genome. EcoRI digestion resulted in a high molecular weight band similar to the band present when no endonuclease was added, suggesting that no EcoRI site was present.

To demonstrate the presence of HPV IU DNA and to exclude the presence of other common genital HPV types, implants were analyzed by DNA in situ hybridization using the whole genomic HPV IU probe, or one of three probe mixes consisting of HPV types 6 and 11, HPV types 16 and 18, and HPV types 31, 33, and 51. Only hybridization with the HPV IU probe resulted in positive signals. No positive signals were present in sections hybridized with the other HPV probe groups, suggesting an absence of these other HPV types in the new implants.

Propagation of HPV IU. To verify that HPV IU could be propagated in the athymic mouse xenograft system, an extract was made from an implant from the initial experiment and used to infect a second human foreskin. Fragments of this foreskin were implanted into 16 athymic mice. Mice were sacrificed after 150 days of growth and implants were removed. of the 32 passaged implants, 20 were significantly larger than the remaining implants and had the same outward extension and demarcation from kidney tissue as appeared in the HPV IU-infected implants from the initial experiment. The remaining 12 implants were spherical and smooth, with the typical appearance of uninfected foreskin implants. Histological analysis of these larger passaged implants was similar to that of the original group of HPV IU implants. Histologic analysis of the smaller implants resembled that of uninfected implants grown in athymic mice. As described above, the DNA sequences of the 452 bp amplimers from passaged, HPV IU-infected implants were identical to those from the original implants.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A recombinant expression vector in which is inserted part or all of an HPV IU genome, ATCC No. PTA-3403, wherein the part is a segment of the HPV IU genome which is an open reading frame selected from the group consisting of E1, E2, E3, E4, E5, E6, E7, L1 and L2.

2. An isolated nucleic acid molecule comprising a genome of a human papillomavirus which is HPV IU, ATCC No. PTA-3403.

3. The nucleic acid molecule of claim 2, wherein the genome comprises SEQ ID NO:1.

4. The nucleic acid molecule of claim 2, which is 8106 bp in length.

5. The nucleic acid molecule of claim 2, comprising a sequence which is the same as nucleotides 6695–7146 of SEQ ID NO:1.

* * * * *

SEQUENCE LISTING

<160> NUMBER OF SEQ ID NOS: 5

<210> SEQ ID NO 1
<211> LENGTH: 8106
<212> TYPE: DNA
<213> ORGANISM: Human Papillomavirus

<400> SEQUENCE: 1

```
atgtcaggag tgcggtaccc caccaacata tttctgctgt gcaaagactg cgaggtggat      60
ttggaagact tacgactgat ttgcatttat tgcacaaatg aattaacaac agcagaagtg     120
ctgtcctttg catggaagga gctgtgtatt aagtgggacc acgaactgcc ctacggagcg     180
tgtgcacagt gtctacgtaa agcagcaaag gtgcgagagc tacggcactg gagccactca     240
agctacgggg caacagtaga agaagaaaca aaaacaccac tggcacagct gtatatacga     300
tgccatatgt gcctgaagcc gttgagtagt caagaaaaag aatatttggt gcaaacaggt     360
gatagacttc ataatatagc aggacagtgg acaggacggt gctgccattg tagggcacca     420
tgcacggcca tacagcaaca atagcagaga ttgtactaga agaaatacca gatatagttg     480
acctatattg taatgaacaa ggtatagaca gctcagagga ggaggatgat agggactgtg     540
gcgtgcgtga ccaactggca gaacaagcaa agcaggccta tagggtgtta acagtgtgtg     600
gtatgtgtgg ccaggcactt agactagcag tgctgtgtga agacgcagac ctaaaacgtc     660
tacaggacct tttggtgaat gcagtggata tagtgtgtcc cggctgtgca taaggacatg     720
gcggatacgg aaggtacaga tactgggact ggggaattta atacagtaac cggggcagga     780
gggtggttta tggtggaagc aatagtggac aaaacaacag gagatacagt gtcaagtgat     840
gaggacgagg agctaacaga taatggagaa gaccttgtag acttttataga cagacacccg     900 ggggatgggc aggaagttcc gttagagctc tttgttcaac aaactgcaga ggatgacgct     960
gcaatagtgc aggcagtaaa acgaaagttt gtatgtagtc ctgcatcaag ttcctgtgca    1020
acatgggtgg acagtgaact aagtccccgt ttggacgcta taaacttaaa tagaagacag    1080
gaaaaggcta gacggaggtt gtttgagcag gacagtgggt atggcaatac gcaggtgaa    1140 actggaacat cagaaagtca ggtacccggg gaaatgaag gcgtgggggg ggctgtggcg    1200
gcacaggaaa cgaggggga ggggcgggag ggggcgacg gcgaatcaca acccgcctgt    1260
gcaggtacag caaacacagg acagagcgcc agaactactg gagctgatcc atgcagtaat    1320
gtaagagccg ccatcttaag taagtttaaa gatttatttg gtctatcatt ttatgatcta    1380
gttagacagt ttaaaagtga taaatccata tgtggagact gggtggtgtg tgcatttggg    1440
```

-continued

```
gtgtactatg ccgtagcaga agctgtgaaa acgttgctgc agccacaatg tttatatgca    1500
catatacagg tgcaagccag ccaatgggga atggtagtac taatgctact aagatttaaa    1560
tgtggcaaaa gccgggaaac agtggctaaa tacatgggta ccgtactaaa tgtacccgaa    1620
aagcatatgc taatagaacc accaaaaata cgtagcgggc catgtgcact atactggtat    1680
agaacagcta tggggaatgc ctcagaagta cttggggaga ccccagagtg gattgtgcga    1740
caaacagtag taggacatgc aatgggagaa gcccaattta gtttatcaat gcttgtgcag    1800
tgggcatatg ataacgatat ccaggaggaa agcgacctag catacgggta tgcacagttg    1860
ggaaatacag atcccaatgc agctgcattt ctagcaagta attgtcaggc aaaatatatt    1920
aaggatgcaa tgacaatgtg taggttgtat cggcgagcgg aacaatccag aatgagtatg    1980
gcacagtgga tagcgcatag ggggcgtaag gtagcagaca caggagattg gaaacatatt    2040
gtgaaatttt taaaatatca aaatgtggaa tttatttcat ttattagtgc atttaaattg    2100
tttttaaagg gagtgcctaa aaaaagctgt ttagtattct atggacctag tgacacaggg    2160
aaatcattgt tttgtatgag cctttttgcaa tacctagggg gcgcagttat atcttatgta    2220
aattcaagca gccatttttg gttgtcccca ttagcagatg ctaaaatagg attgctagat    2280
gatgcaacag cgcaatgctg gacctacata gatgtatatt tgcgcagcat attagatggg    2340
aatccaacaa gcattgatag aaaacataga acactgacac agctaaagtg cccaccacta    2400
atgataacta ctaatgtaga tccactggca gatgagtccc taaagtatca acgcagtagg    2460
attacagtgt ttaaatttt aaacaaatgt ccggtaacca acagcgggga actagtgtac    2520
acactaaata cgaaacctg gaatcattt ttccaaaggt cctgggcacg tttagaattg    2580
catcaagagg aggaggagga ggaggaggag gaggatggca tcgctagccg accgtttaga    2640
tgcgtgccag gagacgctaa tagacctta tgaaaaagat agcaacaagt tggaggacca    2700
gttgttgcat tggcaatgtg tgcgtttgga acatgcaata ttatttaggg caaaggaagc    2760
aggacatgca aaagtaggcc accaggtggt gccaccactt catgtaacca aatcaaaggc    2820
ctgtcaggcc attgcagtcc atttatcgtt gcaaagccta aatgacagtg actttaagca    2880
cgaaccatgg acactgcagg acacatctat ggaaatgtgg aacacacccc cgcagggtg    2940 ctggaagaaa aagggacgca cagtaacagt gagatttgat aaaagtgact gtaatgaaat    3000
ggactatgta agctggggc acatatatgt atatacggag gaaacaagga catggcacaa    3060
agtgtcgggg ggtgtggatt acgcgggact gtattatgag gtgcagggac agaaacagta    3120
ctatgtggag tttgtaaagg aggcccaaaa atatgggacg caaaacatgt gggaggtgca    3180
tgtgggcaac aatgttattc accaaccatg cgactctgta tctagcaccc aggacaccgt    3240
gtgggaagta cccctttgctg caactagtac caggctacca cacaccgcag accccaccgc    3300
cagcacccag gtgctgggcg cccccccagag caccacccaa gtgcagacgc cgcctgtcaa    3360
gcgacagcga ctcctctggg acggacagca gcagcccgac tcaacccaga cagagcacca    3420
aaagcacgtg gacagtggtg cctacggaca cagcagtgac agtgtctgca caaacgccac    3480
aagggacaca gtgaaccgtt accatacacc tgtaatccac ctacaaggtg aaccaaataa    3540
actaaagtgc tttaggtaca gattacataa atcagtacca acattgtttg taagggccac    3600
ctccacatgg cattggacaa gtggggatgc cgccactaaa gcagcatttg taaccttatg    3660
ctatgcaagt atagagcaac gggagctatt tctaaccagg gttacaattc caaagggtat    3720
aaaggcaatg caaggatata tgtctatgtg cttttaactg tacatatgta tatatatata    3780
tagtgtgtaa tacgggtatg taaccaatag tgtataagtg tgtttgcaaa tacctgagcc    3840
```

-continued

```
actatacacc acaccatata ccagtacaac cctggattac atattgtgct tgatttgttt    3900
gtggtgtcat attcttgtgc ttctaatttg cttctggctt tcctacctt ctgcatttgt     3960 ggcatttgtt gtgtttatgt gtatattgta tttggggttg ttattgctat atgtacaagt    4020
attgtggtgt atagggttta tataaccaca caaccagcca ttcactgctg ctacctgtat    4080
atacgtattc cctgtgtatt gtacaatcac tatgtatcca ttggaggcta gaggtggggg    4140
gcaggcatat gatttaattg ttattggccg ggacgaagtg ggattactgc ttattatttt    4200
aattctcatc gtaattatta ttattttgct gtacatgcgg ctactacata tgtaaccacc    4260
tccccttcct gtataccaca tgtagggtat tgttttgtac tgtttgtttt ttactttctt    4320
attggcaata aacatagtta tatatacaat gtcccatgtg cataggcggc gcaaaagggc    4380
gtctgcaact gatttgtacc gtacctgtaa ggttgcaggt acatgccccc ctgatatagt    4440
ccctaaaatt gaaggtgaca catgggccga taggttttta aagtgggcaa gcctggggct    4500 gttcttttgga cggcttggca ttggtacgtc ctctgggcac cggtgttcgg cacaggctat   4560
gtgcccctag gtaccgtcc tcccacggtg gttgacgtag gcccacagc gcgccccct      4620 gtggtcattg aacctgtggg tgccactgaa ccatccattg ttaaccttgt gagggattct    4680
agtgttattg agtctggggc tactatacct acctttacgg gcacacatgg ctttgaggtt    4740
actagttcct ccactacaac ccccgcagta ttggatataa cgccgtcgtc cgccacggta    4800
caggttagca gctctagttt taccaatcct ttatttactg agccgtccat aattgagcct    4860
ccacaacatg gtgacattac aggacatgtg tttactagta ccgctacatc tggtactcac    4920
gggtttgagg aaattccaat gcaaacattt gcaacctctg ggggtacagg ccaggaacct    4980
attagtagta ctcctattcc tggggtacgc cgtgttgcgg gtcctcgcct aggcctttac    5040
agccgtgcca catctcaggt taaggtgcct gattctgcct ttatgtcccg ccctgcatct    5100
tttgtaacat atgacaatcc tgtatttgat cctgatgaaa ctattatatt tgaacaccct    5160
agtttacata atccacccga tcctgatttt ctggatattg tttcattaca taggcctgcc    5220
ttaacagcca gacaaggtac tgtgcgggtg agtcgtgttg gccaaagggc taccttgcgt    5280
acccgtagtg gcaaacaaat cggggcccgt gtacatttct atcatgatat tagccccatt    5340
ccgcccacgg agtccattga gctacagccc ttggaaccct ccgtggcaaa cacctcctta    5400
tatgacatat atgcagatga tgttttttttg gagtcctcgg tgccctgcg gccatccccc    5460 tcatccacct ctgtgtcctt gcagtccact aatgttctg ctacctctgc tgtgactgca    5520
cagtatgaca atgttacagt gccactgtcc cctggattgg atgtacctgc cctttcaggc    5580
cctgacatac acggtgctgc tcatatgcct gcagacccct tgttcctgt gccatctaat    5640 attcctattc agtctgtgtt tatagacggt actgactatt atttattgcc taactacatt    5700
tttttcccta aaaaacgtaa acgtgtgcac tattcttttg cagatggcta tgtgcggcc    5760 tggtgacggc aagacgtact tgcctcccac tcctgtgtct aaggttatca gtacggaccg    5820
ttatgttaca cgcaccaacc tcttttatta cggtggcagc tccagacttc ttaccgtagg    5880
acatccatat tatcctgtac aggttaatgg tcaaggaaaa aaagccacta tccccaaggt    5940
ttctggctac caatataggg tgtttcgcat tagattacct gaccctaata agtttagcct    6000
tcctgatacg tccctatata atcctgacac ggaacgcatg gtatgggcat gccgcggtat    6060
agaggttggt cgtggtcagc ctcttggcgt gggcactagt ggccatcccc tatataatcg    6120
gctggatgac actgaaaaca caccattgct tgctgctgca gacacagata ggcgtgacaa    6180
tgtctcagtg gattacaaac aaacgcagct tattatcatt gggtgtaagc ccccaatagg    6240
```

-continued

```
ggaacactgg gcaaagggta ctgtgtgttc cggtgtgtcc ccgcagcgtg gcgattgtcc      6300
ccccctacag tttgtaaatt ctactataca ggatggcgac atggtggaaa caggctatgg      6360
tgccatggat tttgccacct tacaggaatc taagtctgag gttcctattg atatctgcac      6420
tgccacctgt aaatatcctg attatttaca aatggctgcg gaaccatatg gtgattgtat      6480
gttcttttgc ctccgtaggg aacaaatgtt tgcacgacat tttttttaata ggcatggcac      6540 tatgggcgag gtgctgccta cctcttatta tattccaggc acatctgcta atagtaggaa      6600
cactcttacc agctacatct atgctcctac tcctagtggc tccctggtat cgtccgattc      6660
ccaactattt aataagccct actggctgca tcgtgcccag ggacataata atggcatttg      6720
ttggtttaat gagttatttg ttacagttgt agatactacc cgcagtacca atattactat      6780
ttcagctgct gctacacagg ctaatgaata cacagcctct aactttaagg aatacctccg      6840
ccacacagag gaatatgact tacaggttat attgcaactt tgcaaaatac atctgacccc      6900
tgaaattatg gcatacctac atagtatgaa tgaacattta ttagatgagt ggaattttgg      6960
cgtgttaccg cctccctcca ccagccttga tgatacctat cgctatctgc agtcccgtgc      7020
tattacctgc caaaagggtc cttccgcccc tgcccctaaa aaggatcctt atgatggcct      7080
tgtattttgg gaggttgatt taaaggacaa actatccaca gatttagatc agtttccttt      7140
gggccgtaag tttcttttgc aactgggtcc ccgttctgtg tctgtgtctc gtaagcgccc      7200
tgcctctacc gccccgtctg ccccttctaa gaaaaaggtt aaaaggcgca agtaacatat      7260
gtgtgtgtgt gtttgtgtgt atatctgtgt ttgtgcagtg ttatgcctat atgcggtggt      7320
atgcctttgt gttatgtatg tggcagtacc gttgtatgtg tttgtgtatt atatgtttgt      7380
gcatgtatct gtgttttgtc tgtgtagtat gtgtatgtat ctgtgtgttt tgtatgtgta      7440
tacattgtgg aatgtatgtg ttgtgtgtgc tttaataaac tgtgtgtcat tgtgttgccg      7500
tggactagtc tccggctgcg ccccgtgcag tgtccggctg cacccatga gtaacccctc      7560 catggcacct atgtcctgca ccaccctata gttcctgacc ccgtaggtta ctagttcctt      7620
ttgtgttggc gcgaccggtt tcggtctccc gccttttcgg tctttgcagt ggcacgttgc      7680
cattacacac aatggtaagt aatcccttat taactcatat cctgcatact ttctgtgcca      7740
actatttgca cctgggagtg cctgacagtt tgttggctgc acaatatgat ttttgacag       7800 gcttatattg tacttgtact tcttttgcaa taaaactgct tttaggcaca tacttttcat      7860
gactactttc ccctaagtac tgttttggac atgtagacta ttgcagtagc caactatgtg      7920
tctatccagt aatcctgcag ttctaaactt gttgcacaca cccaggtcgg ttactaccta      7980
cacagcactt tcctttgtaa taatttataa caatcacata gtaaaaaagt agggtgtaac      8040
cgaaatcggt cggaccgagg ggtatacata taaaagggaa gtgtaggctc agcacagcca      8100
ggagct                                                                 8106
```

<210> SEQ ID NO 2
<211> LENGTH: 452
<212> TYPE: DNA
<213> ORGANISM: Human Papillomavirus

<400> SEQUENCE: 2

```
gcccagggac ataataatgg catttgttgg tttaatgagt tatttgttac agttgtagat        60
actacccgca gtaccaatat tactatttca gctgctgcta cacaggctaa tgaatacaca       120
gcctctaact ttaaggaata cctccgccac accgaggaat atgacttaca ggttatattg       180
caactttgca aaatacatct taccccctgaa attatggcat acctacatag tatgaatgaa       240
```

-continued

```
catttattgg atgagtggaa ttttggcgtg ttaccacctc cttccaccag ccttgatgat      300
acctatcgct atctgcagtc ccgtgctatt acctgccaaa agggtccttc cgcccctgcc      360
cctaaaaagg atccttatga tggccttgta ttttgggagg ttgatttaaa ggacaaacta      420
tccacagatt tggatcagta tcctttggga cg                                    452
```

<210> SEQ ID NO 3
<211> LENGTH: 452
<212> TYPE: DNA
<213> ORGANISM: Human Papillomavirus

<400> SEQUENCE: 3

```
gcccagggtc ataataatgg catttgttgg tttaatgagt tatttgttac agttgtagat       60
actacccgca gtaccaatat tactatttca gctgctgcta cacaggctaa tgaatacaca      120
gcctctaact ttaaggaata cctccgccac accgaggaat atgacttaca ggttatattg      180
caactttgca aaatacatct tacccctgaa attatggcat acctacatag tatgaatgaa      240
catttattgg atgagtggaa ttttggcgtg ttaccgcctc cctccaccag ccttgatgat      300
acctatcgct atttgcagtc ccgtgctatt acctgccaaa agggtccttc cgcccctgcc      360
cctaaaaagg atccttatga tggccttgta ttttgggagg ttgatttaaa ggacaaacta      420
tccacagatt tagatcagtt tcctttggga cg                                    452
```

<210> SEQ ID NO 4
<211> LENGTH: 41
<212> TYPE: DNA
<213> ORGANISM: Human Papillomavirus

<400> SEQUENCE: 4

```
cagtaggatc cttatgatgg cttgtatttt gggaggttga t                           41
```

<210> SEQ ID NO 5
<211> LENGTH: 35
<212> TYPE: DNA
<213> ORGANISM: Human Papillomavirus

<400> SEQUENCE: 5

```
gctatggatc cttttttaggg gcagggggcgg aagga                                35
```